US006964987B1

(12) United States Patent
Auguste et al.

(10) Patent No.: US 6,964,987 B1
(45) Date of Patent: *Nov. 15, 2005

(54) HYDROCOLLOID ADHESIVE MASS WITH IMPROVED RESISTANCE TO DETERIORATION OF ITS ABSORPTION CAPACITY AFTER BEING STERILIZED BY RADIATION

(75) Inventors: Stéphane Auguste, Quetigny (FR); Laurent Apert, Dijon (FR); Luc Garima, Dijon (FR)

(73) Assignee: Laboratoires d'Hygiene et de Dietetique, Chenove (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/936,012

(22) PCT Filed: Mar. 9, 2000

(86) PCT No.: PCT/FR00/00582

§ 371 (c)(1),
(2), (4) Date: Sep. 5, 2001

(87) PCT Pub. No.: WO00/53690

PCT Pub. Date: Sep. 14, 2000

(30) Foreign Application Priority Data

Mar. 9, 1999 (FR) .................................. 99 02870

(51) Int. Cl.⁷ .......................... C08L 1/00; C08L 15/00; A61L 15/00; A61F 13/00
(52) U.S. Cl. ...................... 524/35; 523/111; 524/505; 524/522; 424/445; 424/449; 602/54
(58) Field of Search .......................... 523/111; 524/35, 524/505, 522; 424/445, 449; 602/54

(56) References Cited

U.S. PATENT DOCUMENTS

| 3,339,546 | A |   | 9/1967  | Chen |
| 4,231,369 | A |   | 11/1980 | Sorensen et al. |
| 4,551,490 | A |   | 11/1985 | Doyle et al. |
| 4,738,257 | A |   | 4/1988  | Meyer et al. |
| 5,456,745 | A |   | 10/1995 | Roreger et al. |
| 5,633,010 | A | * | 5/1997  | Chen .......................... 424/448 |
| 6,051,748 | A | * | 4/2000  | Auguste et al. ................ 602/54 |
| 6,146,654 | A | * | 11/2000 | Kubo .......................... 424/443 |

FOREIGN PATENT DOCUMENTS

| DE | 42 07 657 A1 | 9/1992 |
| EP | 0 130 061 A1 | 1/1985 |
| EP | 0 730 874 A2 | 9/1996 |
| WO | WO 98/10801 | 3/1998 |
| WO | WO 99/45977 | 9/1999 |

* cited by examiner

*Primary Examiner*—Tae H. Yoon
(74) *Attorney, Agent, or Firm*—Merchant & Gould P.C.

(57) ABSTRACT

The present invention relates to novel hydrocolloid adhesive masses consisting of an adhesive mixture based on a low molecular polyisobutylene and a poly(styrene/olefin/styrene) block polymer, and of a cellulose derivative, with which an acrylate polymer with a glass transition temperature below −20° C. is associated for the purpose of increasing the resistance to deterioration of the absorption capacity of said hydrocolloid adhesive mass after radiosterilization.

The invention further relates to the use of these novel hydrocolloid adhesive masses for medical, dermatological or cosmetic purposes and particularly for the production of dressings for the treatment of blisters, exudative wounds, burns and superficial, deep, chronic or acute dermo-epidermal lesions.

25 Claims, No Drawings

HYDROCOLLOID ADHESIVE MASS WITH IMPROVED RESISTANCE TO DETERIORATION OF ITS ABSORPTION CAPACITY AFTER BEING STERILIZED BY RADIATION

FIELD OF THE INVENTION

The present invention relates to novel hydrocolloid adhesive masses with an improved resistance to deterioration of their absorption capacity after radiosterilization.

More precisely, the present invention relates to novel hydrocolloid adhesive masses consisting of an adhesive mixture based on a low molecular polyisobutylene and a poly(styrene/olefin/styrene) block polymer, and of a hydrocolloid derived from cellulose, with which an acrylate polymer with a glass transition temperature below −20° C. is associated for the purpose of increasing the resistance to deterioration of the absorption capacity of said hydrocolloid adhesive masses after radiosterilization.

The invention further relates to the use of these novel hydrocolloid adhesive masses for medical, dermatological or cosmetic purposes and particularly for the production of dressings for the treatment of blisters, exudative wounds, burns and superficial, deep, chronic or acute dermo-epidermal lesions.

Hydrocolloid adhesive masses based on polyisobutylene, a poly(styrene/olefin/styrene) block copolymer or a mixture of these two polymers have been known for a long time. Such hydrocolloid adhesive masses are described for example in U.S. Pat. No. 3,339,546, U.S. Pat. No. 4,231,369 or U.S. Pat. No. 4,551,490. These hydrocolloid adhesive masses are employed in numerous medical applications, for example as ostomy devices, and for the production of dressings for the treatment of blisters, exudative wounds, burns and superficial, deep, chronic or acute dermo-epidermal lesions.

In order to be used without risk of contamination by microorganisms, it is imperative for all these products, and particularly healing dressings, to be sterile.

Different techniques exist for destroying contaminating microorganisms, such as sterilization with saturated steam or dry heat, sterilization with gas (ethylene oxide, formaldehyde) or sterilization with radiation.

However, they are not all suitable for the manufacture of products, especially products with pharmaceutical applications and particularly those containing hydrocolloid adhesive masses.

Thus sterilization with saturated steam or dry heat cannot be used because the adhesive mass and the hydrocolloid do not readily withstand high temperatures.

Likewise, sterilization with gas is generally avoided because of the risks inherent in the presence of residual gases in dressings. Furthermore, this technique does not allow the sterilizing agent to penetrate the entire volume of the hydrocolloid adhesive mass, thereby limiting its efficacy.

Consequently, the technique generally used for the sterilization of hydrocolloid adhesive masses is sterilization with radiation, which makes it possible to ensure that the product is sterilized to the core, i.e. very effectively. Two types of radiation, namely $\beta$ and $\gamma$ radiation, can be used for this purpose. The sterilizing dose is adjusted according to the initial bioburden, i.e. the quantity of germs present before sterilization.

This ionizing radiation ruptures the double helix of the DNA of bacteria, which are thereby rendered incapable of reproducing, and thus makes it possible to obtain sterile products.

To ensure an effective decontamination with a sufficient safety margin, a mean dose of 25 kgray is generally applied to the products to be sterilized. In practice, a product receives a dose varying between 25 and 45, depending on the process used.

Nevertheless, these two known radiosterilization techniques also have undesirable effects on the hydrocolloid adhesive masses treated. In particular, these rays are sufficiently powerful to break the carbon—carbon and carbon-hydrogen bonds of the adhesive polymers employed and then cause chain ruptures in these macromolecules and reductions in their average molecular weight which influence their cohesive properties in particular.

In the case of adhesive masses based on polyisobutylene, such side effects are well known and are summarized e.g. in chapter 7, "Wound Dressing", particularly pages 165–166, of "Advances in Pressure Sensitive Adhesive Technology—2", published in April 95 by Donatas Satas.

Thus the negative action of irradiation on the cohesion of hydrocolloid adhesive masses leads to adhesive flow phenomena and to the falling-apart or disintegration of the product, particularly when using the product which swells on absorbing the liquids and exudates.

One of the solutions which have been recommended for avoiding this problem is to add a compound for crosslinking said adhesive mass, thereby strengthening its integrity. Thus U.S. Pat. No. 4,738,257 describes the addition of an ethylene/vinyl acetate copolymer to the polyisobutylene, which makes it possible to crosslink the mass during $\gamma$ irradiation. The use of a mixture of a high molecular polyisobutylene and a low molecular polyisobutylene, or the addition of a poly(styrene/isoprene/styrene) or poly(styrene/butadiene/styrene) block polymer to the polyisobutylene, has also been recommended as a solution to the aforementioned problem.

However, this state of the art is silent as regards another undesirable effect resulting from the radiosterilization of hydrocolloid adhesive masses.

It has in fact been found that adhesive masses based on a mixture of polyisobutylene and a poly(styrene/olefin/styrene) block polymer which contain a cellulose derivative, for example sodium carboxymethylcellulose, suffer a substantial loss of absorption capacity after radiosterilization. This loss of absorption, which has not really been explained, could result from degradation of the macromolecular network of the cellulose derivative by the radiation. The substantial decrease in absorption capacity of these hydrocolloid adhesive masses, and the products containing them, after sterilization seems to be just as detrimental as the decrease in cohesion, insofar as it also affects an essential property of these products.

The production of a hydrocolloid adhesive mass consisting of a polyisobutylene, a poly(styrene/olefin/styrene) block copolymer and a cellulose derivative as hydrocolloid, which would have an improved stability or resistance to deterioration of its absorption capacity after irradiation, would therefore constitute a considerable improvement to the existing state of the art.

It has been discovered that this loss of absorption capacity of such hydrocolloid adhesive masses after sterilization can be significantly reduced by the incorporation, into these hydrocolloid adhesive masses, of an acrylate polymer with a glass transition temperature below −20° C.; it is this discovery which forms the basis of the present invention.

Although the mode of action (protection of the cellulose derivative, modification of the phases of the mixture, or some other mode of action) by which this acrylate polymer makes it possible to reduce the deterioration of absorption capacity of these hydrocolloid adhesive masses after irradiation is neither known nor explained, the inventors have demonstrated remarkable results.

The use of such an acrylate polymer with a glass transition temperature below −20° C. for increasing the absorption capacity of a hydrocolloid adhesive mass based on a poly (styrene/olefin/styrene) block copolymer has been described in patent application WO 98/10801. However, said prior art document never addresses the problem of sterilization of the products, and those skilled in the art were unable to discern any useful information as regards the ability of this acrylate polymer significantly to increase the resistance to deterioration of the absorption capacity of a hydrocolloid adhesive mass as described in said document, and a fortiori of an adhesive mass based on polyisobutylene and a poly(styrene/olefin/styrene) block copolymer in which the hydrocolloid also consists specifically of a cellulose derivative, after radiosterilization.

SUBJECTS OF THE INVENTION

Thus, according to a first feature, the present invention relates to a hydrocolloid adhesive mass useful especially for medical purposes, characterized in that said hydrocolloid adhesive mass comprises:
(a) 2 to 15 parts by weight of an acrylate polymer with a glass transition temperature below −20° C.;
(b) 20 to 50 parts by weight of at least one cellulose derivative; and
(c) 32 to 120 parts by weight of an adhesive mixture consisting of at least one low molecular polyisobutylene and a poly(styrene/olefin/styrene) block polymer, with which are associated one or more compounds selected from high molecular polyisobutylenes, polybutenes, sticky or "tackifying" resins, butyl rubbers, plasticizers and antioxidants.

In one currently preferred embodiment, this hydrocolloid adhesive mass comprises:
(a) 2 to 15 parts by weight of an acrylate copolymer with a glass transition temperature below −20° C.;
(b) 20 to 50 parts by weight of a cellulose derivative, especially sodium carboxymethylcellulose;
(c) 10 to 40 parts by weight of a mixture formed of a low molecular polyisobutylene and a poly(styrene/olefin/styrene) block copolymer, especially a poly(styrene/isoprene/styrene);
(d) 20 to 50 parts by weight of a tackifying resin;
(e) 2 to 25 parts by weight of a plasticizer, especially a plasticizing oil; and
(f) 0.1 to 2 parts by weight of at least one antioxidant.

In one particularly preferred embodiment, this hydrocolloid adhesive mass comprises:
(a) 2 to 15 parts by weight of an acrylate polymer with a glass transition temperature of −39° C.;
(b) 20 to 50 parts by weight of sodium carboxymethylcellulose;
(c) 10 to 35 parts by weight of a poly(styrene/olefin/styrene) block copolymer, especially a poly(styrene/isoprene/styrene);
(d) 1 to 20 parts by weight of a low molecular polyisobutylene;
(e) 20 to 50 parts by weight of a tackifying resin;
(f) 2 to 25 parts by weight of a plasticizing oil; and
(g) 0.1 to 2 parts of at least one antioxidant.

In another currently preferred embodiment, this hydrocolloid adhesive mass comprises:
(a) 2 to 15 parts by weight of an acrylate polymer with a glass transition temperature below −20° C.;
(b) 20 to 50 parts by weight of a cellulose derivative, especially sodium carboxymethylcellulose;
(c) 5 to 20 parts by weight of a poly(styrene/olefin/styrene) block polymer, especially a poly(styrene/isoprene/styrene);
(d) 25 to 50 parts by weight of at least one low molecular polyisobutylene;
(e) 2 to 20 parts by weight of a polybutene; and
(f) 0.1 to 2 parts by weight of at least one antioxidant.

According to a second feature, the present invention relates to the use of these hydrocolloid adhesive masses for the production of dressings, especially for the treatment of blisters, superficial, deep, chronic or acute dermo-epidermal lesions, exudative wounds and burns.

The compounds used to produce the adhesive mixture of the hydrocolloid adhesive masses according to the invention are the ones normally used by those skilled in the art to prepare adhesive masses, and reference may be made in this connection to the above-mentioned prior art document for the definitions of all the compounds used and also their respective proportions for obtaining the desired adhesive and mechanical properties.

Thus, within the framework of the present invention, block copolymers of the poly(styrene/olefin/styrene) type which may be used are copolymers in which the olefin blocks can consist of isoprene, butadiene, ethylene/butylene or ethylene/propylene units and mixtures thereof. Poly(styrene/isoprene/styrene) three-block copolymers are preferred among these copolymers.

Poly(A/B/A) three-block copolymer of the poly(styrene/isoprene/styrene) type [abbreviated to poly(SIS)] is understood here as meaning a poly(SIS) material with a styrene content of between 14 and 52% by weight, based on the weight of said poly(SIS). This expression also covers poly (SIS) materials containing a mixture of poly(SIS) three-block copolymers and two-block copolymers of the poly (styrene/isoprene) type.

Such products, which are well known to those skilled in the art, are marketed for example by SHELL and EXXON CHEMICAL under the names KRATON® D and VECTOR® respectively.

Within the framework of the present invention, three-block copolymers with a styrene content of between 14 and 30% by weight, based on the weight of said poly(SIS), are preferred. The products marketed by EXXON CHEMICAL under the names VECTOR® 4114 and VECTOR® 4113 and by SHELL CHEMICALS under the names KRATON® D-1111CS, KRATON® D-1107 or KRATON® 1161 will be particularly preferred.

The product marketed by SHELL CHEMICALS under the name KRATON® D-1102, for example, may be mentioned among the poly(styrene/butadiene/styrene) copolymers.

Within the framework of the present invention, polyisobutylenes which may be used are those with a low molecular weight in the order of 40,000 to 80,000 daltons, such as the compounds marketed by EXXON CHEMICAL under the name VISTANEX® or by BASF under the name OPPANOL®.

The products marketed under the names VISTANEX® LM-MS, VISTANEX® LM-MH, OPPANOL® B12 and OPPANOL® B15 will be particularly preferred.

These products may be used by themselves or in a mixture.

A variety of additional compounds are generally added to the association of polyisobutylene and poly(styrene/olefin/styrene) in order to produce an adhesive mixture which affords hydrocolloid adhesive masses with optimized properties of elasticity, adhesion, stability over time, and cohesion.

These two compounds are thus generally associated, in the hydrocolloid adhesive masses, with stabilizers such as antioxidants, adhesion improvers such as "tackifying" resins, plasticizers such as polybutenes or plasticizing oils, or cohesion improvers such as butyl rubbers or high molecular polyisobutylenes, etc.

Such compositions are thus defined in chapter 7, "Wound Dressings", pages 158 to 171, of "Advances in Pressure Sensitive Adhesive Technology—2", published in April 95 by Donatas Satas, as cited above.

Such formulations are also described for example in patent application EP-A-130061.

It is thus possible to add polyisobutylenes with a high molecular weight in the order of 400,000 to 2,000,000 daltons, for example the products marketed by EXXON CHEMICAL under the names VISTANEX® L-80 or VISTANEX® L100.

Among the tackifying resins suitable for the production of these adhesive mixtures, there may thus be mentioned the resins generally employed in the field of adhesives by those skilled in the art, such as modified polyterpene or terpene resins, hydrogenated rosin resins, polymerized rosin resins, rosin ester resins, hydrocarbon resins, mixtures of aromatic and aliphatic resins, etc. A synthetic resin formed of $C_5/C_9$ copolymers and marketed by GOOD YEAR under the name WINGTACK® 86 will be particularly preferred within the framework of the present invention.

Likewise, antioxidants are understood as meaning the compounds commonly employed by those skilled in the art for ensuring that the compounds used in the formulation of the matrices, particularly the tackifying resins and the block copolymers, are stable towards oxygen, heat, ozone and ultraviolet radiation. It is possible to use one or more of these antioxidants in association.

Appropriate antioxidants which may be mentioned are phenolic antioxidants, for example the products marketed by CIBA-GEIGY under the names IRGANOX® 1010, IRGANOX® 565 and IRGANOX® 1076, and sulfur-containing antioxidants, for example the zinc dibutyldithiocarbamate marketed by AKZO under the name PERKACIT® ZDBC.

The association of IRGANOX® 1010 and PERKACIT® ZDBC will be preferred within the framework of the present invention.

Any type of plasticizer normally used by those skilled in the art for preparing hydrocolloid adhesive masses based on a poly(styrene/olefin/styrene) block copolymer or polyisobutylene can be employed. Plasticizers such as polybutenes, for example those marketed by BP CHEMICALS under the name NAPVIS® 10, plasticizing oils or phthalate derivatives such as dioctyl phthalate, can thus be incorporated into these adhesive masses.

Plasticizing oils will preferably be used within the framework of the present invention.

Plasticizing oils are understood here as meaning the mineral or vegetable oils commonly employed by those skilled in the art for plasticizing the block copolymers of the styrene/olefin/styrene type or the polyisobutylene used in the composition of the adhesive mixtures employed in hydrocolloid adhesive masses.

The mineral oils generally used are mixtures of compounds of a paraffinic, naphthenic or aromatic nature in variable proportions.

Examples of plasticizing oils which may thus be mentioned are the products marketed by SHELL under the names ONDINA® and RISELLA® in the case of mixtures based on naphthenic and paraffinic compounds, or under the name CATENEX® in the case of mixtures based on naphthenic, aromatic and paraffinic compounds.

The mineral plasticizing oil marketed under the name ONDINA® 68 will be particularly preferred within the framework of the present invention.

Cellulose derivatives are understood here as denoting the cellulose compounds commonly used in hydrocolloid adhesive masses by those skilled in the art, said compounds having a capacity to absorb the hydrophilic liquids and the exudates and to transport them rapidly.

These cellulose derivatives are cellulose polymers such as hydroxyethyl celluloses, hydroxypropyl celluloses, carboxymethyl celluloses and their alkali metal salts such as the sodium or calcium salts. These cellulose derivatives may be used by themselves or in association.

The alkali metal salts of carboxymethyl cellulose, particularly sodium carboxymethylcellulose, will be preferred within the framework of the present invention. The sodium carboxymethylcelluloses marketed by AQUALON under the names BLANOSE® 7H4XF, BLANOSE® 7H3XF and AQUASORB® A500 may thus be mentioned as examples.

The acrylate polymers suitable for carrying out the invention are pressure-sensitive acrylate compounds with a glass transition temperature (Tg) below −20° C.

Such acrylate compounds are copolymers formed of:
either at least one monomer selected from the group consisting of acrylic acid alkyl esters in which the linear or branched alkyl group of the ester contains 1 to 18 carbon atoms, preferably 4 to 10 carbon atoms and particularly 4 to 8 carbon atoms, for example methyl, ethyl, n-propyl, n-butyl, isobutyl, n-hexyl, 2-ethylhexyl, n-octyl, isooctyl, n-decyl and n-dodecyl acrylates, associated with acrylic acid;

or at least two monomers selected from the group consisting of acrylic acid alkyl esters in which the linear or branched alkyl group of the ester contains 1 to 18 carbon atoms, preferably 4 to 10 carbon atoms and particularly 4 to 8 carbon atoms, for example methyl, ethyl, n-propyl, n-butyl, isobutyl, n-hexyl, 2-ethylhexyl, n-octyl, isooctyl, n-decyl and n-dodecyl acrylates.

The respective percentages or proportions of these different monomers are adjusted to give a copolymer with the desired glass transition temperature, i.e. below −20° C.

A copolymer containing at least one monomer selected from n-butyl acrylate, 2-ethylhexyl acrylate and isooctyl acrylate, copolymerized with acrylic acid, will preferably be used within the framework of the present invention.

Copolymers containing from 1 to 20% and preferably 1 to 10% by weight of acrylic acid, expressed relative to the total weight of all the monomers, will be very particularly preferred.

Such acrylate compounds can also be homopolymers whose constituent monomer is selected from the group consisting of acrylic acid alkyl esters in which the alkyl group of the ester is either a linear alkyl group containing 2 to 12 carbon atoms or an isobutyl, 2-ethylhexyl or isooctyl group.

Among these homopolymers, poly-n-butyl acrylate will be preferred within the framework of the present invention.

According to one particular characteristic of the invention, the products well known to those skilled in the art for their use in a solventless coating process, known as a hot melt process, will be chosen.

The products marketed by BASF under the following names may thus be mentioned as examples:

ACRONAL® A150F (an n-butyl acrylate homopolymer with a glass transition temperature of −41° C.), ACRONAL® DS3435X (an n-butyl acrylate homopolymer with a glass transition temperature of 46° C.), ACRONAL® DS3429 (an n-butyl acrylate/2-ethylhexyl acrylate/acrylic acid copolymer with a glass transition temperature of −31° C.), and ACRONAL® DS3458 (an n-butyl acrylate/acrylic acid copolymer with a glass transition temperature of −39° C.).

The product marketed by MONSANTO under the name MODAFLOW® (an ethyl acrylate/2-ethylhexyl acrylate copolymer) may also be mentioned.

The acrylate polymer marketed under the name ACRONAL® DS3458 will be very particularly preferred within the framework of the present invention.

The hydrocolloid adhesive mass according to the invention is particularly useful for any medical applications in which the product containing said mass has to be sterilized. Thus there may be mentioned the production of dressings and bandages for the treatment of blisters, superficial, deep, chronic or acute dermo-epidermal lesions, exudative wounds and burns, and the production of adhesive joints employed in ostomy.

Within the context of these applications, various products of a dermatological, cosmetological or therapeutic nature can be added to the formulation of the hydrocolloid adhesive mass, examples being antifungals, antimicrobials or antibacterials such as sulfadiazine silver, pH regulators, healing accelerators, vitamins, plant extracts, trace elements, local anesthetics, odor traps, menthol, methyl salicylate, hormones, anti-inflammatories, etc.

Within the context of the production of a dressing for the treatment of blisters or the treatment or protection of wounds, different categories of dermo-epidermal lesions, burns and bedsores, the hydrocolloid adhesive mass according to the invention is coated onto an appropriate support in the desired weight per unit area, according to the techniques known to those skilled in the art, by a solvent phase process or, preferably, by a hot melt process, i.e. a solventless process, at a temperature of between 110 and 160° C.

The support is chosen as a function of the required properties (leaktightness, elasticity, etc.), depending on the type of dressing and the intended application.

It can take the form of a monolayer or multilayer film with a thickness varying from 5 to 150 µm, or a nonwoven or a foam with a thickness of 10 to 500 µm.

These supports based on synthetic or natural materials are the ones generally used by those skilled in the art in the field of dressings and the medical applications mentioned above.

Thus there may be mentioned foams made of polyethylene, polyurethane or PVC, and nonwovens made of polypropylene, polyamide, polyester, ethyl cellulose, etc.

It will be preferable, however, to use films as supports, especially poly-urethane films such as the products marketed by Smith and Nephew under the reference LASSO, or polyurethane films produced from the polyurethane marketed by B. F. GOODRICH under the name ESTANE, low density polyethylene films such as those marketed by SOPAL, films based on a thermoplastic polyether/polyester copolymer, such as the products marketed by DUPONT DE NEMOURS under the trade mark Hytrel®, or composite films based on polyurethane and a nonwoven.

The dressings produced from the hydrocolloid adhesive mass according to the invention can have any geometric shape, i.e. square, rectangular, circular or oval. Likewise, they can be of any size, which will be adapted according to the surface area of the part to be treated or protected.

In practical terms, the surface of the hydrocolloid adhesive mass which is not bonded to the support may be covered with a protective layer or film to be peeled off before the dressing is used.

The assembly formed in this way may itself be packaged in a leaktight protection, for example made of polyethylene/aluminum composites, or in blister packs.

The advantages, characteristics and applications of the invention will be understood more clearly from the following description of Examples and comparative tests.

Of course, these data as a whole do not in any way imply a limitation but are given by way of illustration.

The following abbreviations have been used hereafter for the sake of convenience:

SIS: poly(styrene/isoprene/styrene) three-block copolymer

EXAMPLE 1

12.5 kg of ONDINA® 68 (a mineral oil marketed by SHELL), 14.2 kg of VECTOR® 4114 (an SIS copolymer marketed by DEXCO), 3.55 kg of VISTANEX® LM-MH (a low molecular PIB polymer marketed by EXXON CHEMICAL), 0.4 kg of PERKACIT® ZDBC (zinc dibutyldithiocarbamate, an antioxidant marketed by AKZO) and 0.4 kg of IRGANOX® 1010 (an antioxidant marketed by CIBA-GEIGY) are introduced successively into a Z-blade mixer at a temperature in the order of 140° C. The mixture obtained is mixed at between 120 and 140° C. for about 30 minutes. 6.5 kg of ACRONAL® DS3458 (a butyl acrylate/acrylic acid copolymer marketed by BASF) are then added and the mixture obtained is mixed for 40 minutes, still at around 140° C. 26.75 kg of WINGTACK® 86 (a tackifying resin marketed by GOOD YEAR) are then added and the mixture is mixed for 40 minutes, still at around 140° C. Finally, 35.7 kg of BLANOSE® 7H4XF (a sodium carboxymethylcellulose marketed by AQUALON) are introduced and mixing is continued for 40 minutes, still at around 140° C. The resulting mixture is coated onto a film of siliconized paper at a rate of 1000 g/m² at a temperature of between 120 and 160° C. The coating produced in this way is transferred to a 30 µm thick, polyurethane final support (produced from a polyurethane marketed by UCB under the name UCE-COAT®). Shapes of the appropriate dimensions are then cut out and packaged in heat-sealing sachets or in blister packs.

COMPARATIVE EXAMPLE 1

13.95 kg of ONDINA® 68, 15.8 kg of VECTOR® 4114, 3.95 kg of VISTANEX® LM-MH, 0.4 kg of PERKACIT® ZDBC and 0.4 kg of IRGANOX® 1010 are introduced successively into a Z-blade mixture at a temperature in the order of 140° C. The mixture obtained is mixed for about 30 minutes at about 140° C. 29.8 kg of WINGTACK® 86 are then introduced and mixing is continued for about 35 minutes, still at 140° C. Finally, 35.7 kg of BLANOSE® 7H4XF are introduced and mixing is continued for 45 minutes at around 140° C. The resulting mixture is coated onto a film of siliconized paper at a rate of 1000 g/m² at a temperature of between 120 and 160° C. The coating produced in this way is transferred to a 30 µm thick, polyurethane final support (produced from a polyurethane marketed by UCB under the name UCECOAT®). Shapes of the appropriate dimensions are then cut out and packaged in heat-sealing sachets or in blister packs.

Tests

To demonstrate the resistance to deterioration of the absorption capacity of the hydrocolloid adhesive masses according to the invention after irradiation, absorption measurements were made on a product according to the invention (Example 1) containing an acrylate polymer with a glass transition temperature below −20° C., and on the same product not containing the latter (Comparative Example 1), before β radiosterilization and after β radiosterilization at different irradiation doses.

The absorption measurements were made according to the following protocol:

The sample used is produced as described in Example 1 and in Comparative Example 1, being formed of the final support, the hydrocolloid adhesive mass and the film of siliconized paper serving as a peel-off protector, which is cut to produce an adhesive tape. The measurement is made using a measuring cell consisting of an aluminum cylinder on which a test sample of the adhesive tape is placed and to which a support is subsequently fixed in order to hold the cylinder/sample assembly firmly together. The peripheral part of this support has a siliconized joint to which the peripheral section of the sample sticks when pressed on.

The absorption is measured by the difference in weight of the support/adhesive tape/cylinder assembly before and after the sample has been brought into contact for a fixed period of time, in this case 24 hours, with a reference liquid.

In the following tests, the reference liquid is a solution of Dextran D4876 (marketed by Sigma) containing 60 g per liter in 0.15 molar sodium chloride solution.

The measurements are made as follows:
1) a test sample (e.g. of 16 cm² in this case) of the adhesive tape is cut out and the protective film is removed;
2) the sample is incorporated into the measuring cell as described above;
3) the resulting assembly is weighed; let $P_0$ be the weight obtained;
4) 20 ml of the preprepared reference liquid are then introduced into the cylinder;
5) the assembly is left in contact with the liquid at 23° C. for 24 hours;
6) when these 24 hours have elapsed, the support/sample/cylinder assembly is reweighed after removal of the unabsorbed solution; let $P_1$ be the weight obtained;
7) the absorption capacity, corresponding to the surface absorption, is calculated using the following formula: Absorption=$4(P_1-P_0)/\pi D^2$, where D is the diameter of the cylinder, i.e. 0.0357 m in this case.

The absorption, expressed in g/m², is thus defined here by:

Absorption=$(P_1-P_0)10^3$

Each test is performed at least 5 times.

The absorption capacity obtained is the mean of these different attempts.

Sterilization with β radiation is effected in conventional manner. The products to be sterilized move past on a conveyor belt and the treatment dose applied is adjusted by varying the speed of the conveyor.

The products of Example 1 and Comparative Example 1 were thus treated at the following doses: 15, 25, 35 and 45 kilograys.

All the absorption results for these different doses are collated in Table I, in which:
A(EX1) and A(CE1) represent the absorptions at 24 hours, expressed in g/m², of the adhesive tapes obtained according to Example 1 and according to Comparative Example 1 respectively, and
R, expressed as a percentage, represents the ratio of the absorption of a sterilized adhesive tape to the absorption of the same but unsterilized adhesive tape, for each irradiation dose.

TABLE I

|  | Unsterilized | 15 KGY | 25 KGY | 35 KGY | 45 KGY |
| --- | --- | --- | --- | --- | --- |
| A(EX1) | 5590 | 4880 | 4520 | 4260 | 3950 |
| R | — | 87.3 | 80.8 | 72.2 | 70.7 |
| A(CE1) | 1820 | 620 | 430 | 460 | 400 |
| R | — | 34 | 23.6 | 25.2 | 22 |

Analysis of Table I provides a perfect illustration of the value of using an acrylate copolymer with a glass transition temperature below −20° C. for increasing the resistance to deterioration, after radiosterilization, of the absorption capacity of a hydrocolloid adhesive mass formed of an adhesive mixture based on polyisobutylene and a poly (styrene/olefin/styrene) block copolymer, in this case a poly (styrene/isoprene/styrene), and of a cellulose derivative, in this case sodium carboxymethylcellulose.

It is in fact found that at an irradiation dose of as little as 15 kilograys, which is less than the dose of 25 kilograys generally used for sterilizing the products with a safety margin, the value R, which represents the percentage of residual absorption relative to the unsterilized adhesive mass, is 87.3% for the hydrocolloid adhesive mass containing the acrylate polymer (Example 1), compared with only 34% in the absence of the latter (Comparative Example 1).

Similarly, this ratio is 80.8% compared with 23.6% at 25 kilograys, 72.2% compared with 25.2% at 35 kilograys and 70.7% compared with 22% at 45 kilograys.

Given that, in practice, when an industrial lot is radiosterilized, a product receives a dose ranging from 25 to 45 kilograys, the value of the present invention is understood since the addition of an acrylate polymer to the hydrocolloid adhesive mass makes it possible to retain ¾ of the initial absorption compared with only ¼ for the same product without acrylate polymer, in this dosage range.

This result constitutes a significant advance in the field of adhesive masses in which the hydrocolloid is a cellulose derivative. In fact, the commercial product thus obtained has a good absorption level without requiring the use of mixtures with other kinds of hydrocolloid, for example gums, pectin or gelatin.

This is all the more important because the use of compounds of animal origin, such as gelatin, could present problems, especially in pharmaceutical products. The present invention thus makes it possible to produce simpler hydrocolloid adhesive masses based on polyisobutylene and poly(styrene/olefin/styrene) in which the risks of incompatibility between the compounds is reduced and in which it is therefore easier to optimize the properties of adhesion, cohesion and absorption.

What is claimed is:

1. Hydrocolloid adhesive mass for medical purposes, which comprises:
(a) 2 to 15 parts by weight of an acrylate polymer with a glass transition temperature below −20° C.;

(b) 20 to 50 parts by weight of one or more cellulose derivative; and (c) 32 to 120 parts by weight of an adhesive mixture consisting of one or more low molecular polyisobutylene and one or more poly(styrene/olefin/styrene) block polymer, with which are associated one or more compounds selected from the group consisting of high molecular polyisobutylenes, polybutenes, sticky or "tackifying" resins, butyl rubbers, plasticizers and antioxidants.

2. Hydrocolloid adhesive mass according to claim 1, wherein the acrylate polymer with a glass transition temperature below −20° C. is a copolymer formed of at least one monomer selected from the group consisting of acrylic acid alkyl esters in which the linear or branched alkyl group of the ester has 1 to 18 carbon atoms, copolymerized with acrylic acid.

3. Hydrocolloid adhesive mass according to claim 1, wherein the acrylate polymer with a glass transition temperature below −20° C. is a copolymer formed of at least one monomer selected from the group consisting of acrylic acid alkyl esters in which the linear or branched alkyl group of the ester has 4 to 10 carbon atoms, copolymerized with acrylic acid.

4. Hydrocolloid adhesive mass according to claim 1, wherein the acrylate polymer with a glass transition temperature below −20° C. is a copolymer formed of at least one monomer selected from the group consisting of acrylic acid alkyl esters in which the linear or branched alkyl group of the ester has 4 to 8 carbon atoms, copolymerized with acrylic acid.

5. Hydrocolloid adhesive mass according to claim 2, wherein the above-mentioned acrylate copolymer is a copolymer formed of at least one monomer selected from the group consisting of n-butyl acrylate, 2-etylhexyl acrylate and isooctyl acrylate, copolymerized with acrylic acid.

6. Hydrocolloid adhesive mass according to claim 2, wherein the above-mentioned acrylate copolymer is selected from the group consisting of an n-butyl acrylate/acrylic acid copolymer with a glass transition temperature of −39° C. and an n-butyl acrylate/2-ethylhexyl acrylate/acrylic acid copolymer with a glass transition temperature of −31° C.

7. Hydrocolloid adhesive mass according to claim 5, wherein the above-mentioned acrylate copolymer comprises from 1 to 20% by weight of acrylic acid, expressed relative to the total weight of all the monomers.

8. Hydrocolloid adhesive mass according to claim 1, wherein the acrylate polymer with a glass transition temperature below −20° C. is a copolymer formed of at least two monomers selected from the group consisting of acrylic acid alkyl esters in which the linear or branched alkyl group of the ester contains 1 to 18 carbon atoms.

9. Hydrocolloid adhesive mass according to claim 1, wherein the acrylate polymer with a glass transition temperature below −20° C. is a copolymer formed of at least two monomers selected from the group consisting of acrylic acid alkyl esters in which the linear or branched alkyl group of the ester contains 4 to 10 carbon atoms.

10. Hydrocolloid adhesive mass according to claim 1, wherein the acrylate polymer with a glass transition temperature below −20° C. is a copolymer formed of at least two monomers selected from the group consisting of acrylic acid alkyl esters in which the linear or branched alkyl group of the ester contains 4 to 8 carbon atoms.

11. Hydrocolloid adhesive mass according to claim 1, wherein the acrylate polymer with a glass transition temperature below −20° C. is a homopolymer whose constituent monomer is selected from the group consisting of acrylic acid alkyl esters in which the alkyl group of the ester is selected from the group consisting of a linear alkyl group containing 2 to 12 carbon atoms, isobutyl, 2-ethylhexyl and isooctyl group.

12. Hydrocolloid adhesive mass according to claim 1, wherein the acrylate polymer with a glass transition temperature below −20° C. is a homopolymer whose constituent monomer is an n-butyl acrylate homopolymer with a glass transition temperature of 41° C.

13. Hydrocolloid adhesive mass according to claim 1, which comprises:
(a) 2 to 15 parts by weight of an acrylate copolymer with a glass transition temperature below −20° C.;
(b) 20 to 50 parts by weight of a cellulose derivative;
(c) 10 to 40 parts by weight of a mixture formed of a low molecular polyisobutylene and a poly(styrene/olefin/styrene) block copolymer;
(d) 20 to 50 parts by weight of a tackifying resin;
(e) 2 to 25 parts by weight of a plasticizer; and
(f) 0.1 to 2 parts by weight of at least one antioxidant.

14. Hydrocolloid adhesive mass according to claim 1, which comprises:
(a) 2 to 15 parts by weight of an acrylate copolymer with a glass transition temperature below −20° C.;
(b) 20 to 50 parts by weight of sodium carboxymethylcellulose;
(c) 10 to 40 parts by weight of a mixture formed from a low molecular weight polyisobutylene and a poly(styrene/styrene/styrene);
(d) 20 to 50 parts by weight of a tackifying resin;
(e) 2 to 25 parts by weight of a plasticizing oil; and
(f) 0to 2 parts by weight of at least one antioxidant.

15. Hydrocolloid adhesive mass according to claim 13, wherein the above-mentioned plasticizer is a mineral plasticizing oil selected from the group consisting of naphthenic, paraffinic and aromatic compounds.

16. Hydrocolloid adhesive mass according to claim 13, which comprises:
(a) 2 to 15 parts by weight of an acrylate polymer with a glass transition temperature of −39° C.;
(b) 20 to 50 parts by weight of sodium carboxymethylcellulose;
($c_1$) 10 to 35 parts by weight of a poly(styrene/olefin/styrene) block copolymer;
($c_2$) 1 to 20 parts by weight of a low molecular polyisobutylene;
(d) 20 to 50 parts by weight of a tackifying resin;
(e) 2 to 25 parts by weight of a plasticizing oil; and
(f) 0.1 to 2 parts of at least one antioxidant;
wherein the total amount of low molecular weight polyisobutylene and poly(styrene/olefin/styrene) block copolymer is less than 40 parts by weight.

17. Hydrocolloid adhesive mass according to claim 1, which comprises.
(a) 2 to 15 parts by weight of an acrylate polymer with a glass transition temperature below −20° C.;
(b) 20 to 50 parts by weight of a cellulose derivative;
(c) 5 to 20 parts by weight of a poly(styrene/olefin/styrene) block polymer;
(d) 25 to 50 parts by weight of at least one low molecular polyisobutylene;
(e) 2 to 20 parts by weight of a polybutene; and
(f) 0.1 to 2 parts by weight of at least one antioxidant.

18. Hydrocolloid adhesive mass according to claim 1, which comprises:

(a) 2 to 15 parts by weight of an acrylate copolymer with a glass transition temperature below −20° C.;
(b) 20 to 50 parts by weight of sodium carboxymethylcellulose;
(c) 10 to 40 parts by weight of a mixture formed from a low molecular weight polyisobutylene and a poly(styrene/isoprene/styrene);
(d) 20 to 50 parts by weight of a tackifying resin;
(e) 2 to 20 parts by weight of a polybutene; and
(f) 0.1 to 2 parts by weight of at least one antioxidant.

19. Hydrocolloid adhesive mass according to claim 1, wherein the above-mentioned block copolymer is a poly (styrene/isoprene/styrene) with a styrene content of between 14 and 52% by weight, based on the weight of said copolymer.

20. Hydrocolloid adhesive mass according to claim 1, wherein the cellulose derivative is an alkali metal salt of carboxymethyl cellulose.

21. A dressing for the treatment of blisters, superficial, deep, chronic or acute dermo-epidermal lesions, exudative or burns, said dressing being formed of a support onto which an hydrocolloid adhesive mass according to claim 1 is coated.

22. A dressing for the treatment of blisters, superficial, deep, chronic or acute dermo-epidermal lesions, exudative or burns, said dressing being formed of a support onto which an hydrocolloid adhesive mass according to claim 17 is coated.

23. A dressing for the treatment of blisters, superficial, deep, chronic or acute dermo-epidermal lesions, exudative or burns, said dressing being formed of a support onto which an hydrocolloid adhesive mass according to claim 8 is coated.

24. A dressing for the treatment of blisters, superficial, deep, chronic or acute dermo-epidermal lesions, exudative or burns, said dressing being formed of a support onto which an hydrocolloid adhesive mass according to claim 13 is coated.

25. A dressing for the treatment of blisters, superficial, deep, chronic or acute dermo-epidermal lesions, exudative or burns, said dressing being formed of a support onto which an hydrocolloid adhesive mass according to claim 16 is coated.

* * * * *

UNITED STATES PATENT AND TRADEMARK OFFICE
CERTIFICATE OF CORRECTION

| | | |
|---|---|---|
| PATENT NO. | : 6,964,987 B1 | Page 1 of 1 |
| APPLICATION NO. | : 09/936012 | |
| DATED | : November 15, 2005 | |
| INVENTOR(S) | : Auguste et al. | |

It is certified that error appears in the above-identified patent and that said Letters Patent is hereby corrected as shown below:

Front page, (56) References Cited, Other Documents: Insert --Satas. Advances in Pressure Sensitive Adhesive Technology-2. April 1995--

Col. 7, line 10: "temperature of 46° C.)," should read --temperature of -46° C.),--

Col. 11, line 35, claim 5: "acrylate, 2-ethylhexyl acrylate" should read --acrylate, 2-ethylhexyl acrylate--

Col. 12, line 10, claim 12: "temperature of 41° C." should read --temperature of -41° C.--

Col. 12, line 30, claim 14: "rene/styrene/styrene);" should read --rene/isoprene/styrene;--

Col. 12, line 33, claim 14: "0to 2 parts" should read --0.1 to 2 parts--

Signed and Sealed this

Twenty-fifth Day of July, 2006

JON W. DUDAS
*Director of the United States Patent and Trademark Office*